United States Patent
Mori et al.

(10) Patent No.: US 7,860,471 B2
(45) Date of Patent: Dec. 28, 2010

(54) BODY-INSERTABLE APPARATUS

(75) Inventors: Takeshi Mori, Tokyo (JP); Takemitsu Honda, Tokyo (JP); Masatoshi Homan, Tokyo (JP)

(73) Assignee: Olympus Corporation, Tokyo (JP)

( * ) Notice: Subject to any disclaimer, the term of this patent is extended or adjusted under 35 U.S.C. 154(b) by 1030 days.

(21) Appl. No.: 11/595,052

(22) Filed: Nov. 9, 2006

(65) Prior Publication Data

US 2007/0083083 A1    Apr. 12, 2007

Related U.S. Application Data

(63) Continuation of application No. PCT/JP2005/007407, filed on Apr. 18, 2005.

(30) Foreign Application Priority Data

May 10, 2004  (JP)  ............... 2004-139892

(51) Int. Cl.
*H04B 1/18* (2006.01)
(52) U.S. Cl. ............... 455/151.2; 348/68; 348/65; 348/70; 348/71; 455/100
(58) Field of Classification Search ............... 348/68, 348/65; 455/100
See application file for complete search history.

(56) References Cited

U.S. PATENT DOCUMENTS 5,019,912 A * 5/1991 Matsuda ............... 348/240.2
5,408,265 A * 4/1995 Sasaki ............... 348/70
5,604,531 A    2/1997 Iddan et al.
7,009,634 B2 * 3/2006 Iddan et al. ............... 348/76
7,511,733 B2 * 3/2009 Takizawa et al. ............... 348/68

FOREIGN PATENT DOCUMENTS

| JP | 10-303802 | 11/1998 |
| JP | 2001-245844 | 9/2001 |
| JP | 2001-304879 | 10/2001 |
| JP | 2002-345743 | 12/2002 |
| JP | 2003-008980 | 1/2003 |
| WO | WO 01/39401 A1 | 5/2001 |

* cited by examiner

*Primary Examiner*—Nay A Maung
*Assistant Examiner*—Richard Chan
(74) *Attorney, Agent, or Firm*—Scully, Scott, Murphy & Presser, P.C.

(57) ABSTRACT

A body-insertable apparatus is inserted into a subject and obtains information of an inside of the subject. The body-insertable apparatus includes an illuminating unit that outputs an illumination light to illuminate the inside of the subject; an imaging unit that obtains image information of the inside of the subject which is illuminated by the illuminating unit; a radio transmitting unit that transmits information of the inside of the subject by radio; a clock generating unit that generates a clock for obtainment of the image information by the imaging unit; and a correcting unit that corrects a clock for radio transmission by the radio transmitting unit based on the clock generated by the clock generating unit.

8 Claims, 5 Drawing Sheets

BODY-INSERTABLE APPARATUS

CROSS-REFERENCE TO RELATED APPLICATIONS

This application is a continuation of PCT international application Ser. No. PCT/JP2005/007407 filed Apr. 18, 2005 which designates the United States, incorporated herein by reference, and which claims the benefit of priority from Japanese Patent Application No. 2004-139892, filed May 10, 2004, incorporated herein by reference.

BACKGROUND OF THE INVENTION

1. Field of the Invention

The present invention relates to a body-insertable apparatus, such as a swallowable capsule endoscope, which is insertable inside a subject and generates a transmission carrier wave when transmitting image information by radio from inside the subject.

2. Description of the Related Art

In a field of microscope, some capsule endoscopes come to be equipped with an imaging function and a radio function in recent years. The capsule endoscope is swallowed by a patient, i.e., a subject, for an observation (examination), travels inside organs (body cavities) such as a stomach and small intestine of the subject following peristaltic movements, and is naturally discharged from a living body of the subject (human body). During an observation period, i.e., a time period after the swallowing up to the discharging, the capsule endoscope sequentially images inside the subject using the imaging function thereof.

During the observation period, i.e., while the capsule endoscope travels inside the organs, image data obtained inside the body cavity by the capsule endoscope is sequentially transmitted by the radio function, e.g., by radio transmission, to an external device arranged outside the subject, and stored in a memory of the external device. When the patient carries the external device having such radio function and memory function, the patient can freely move without inconvenience after swallowing the capsule endoscope until discharging the same. When the observation by the endoscope is completed, a doctor or a nurse can display the image inside the body cavity on a display unit such as a monitor based on the image data stored in the memory of the external device and make diagnosis.

One type of the above-described capsule endoscope is described in Japanese Patent Laid-Open No. 2002-345743, for example. The swallowable capsule endoscope of Patent Document 1 incorporates a battery for power supply. An LED generates an illumination light by electricity supplied from the battery. The illumination light is directed to and reflected by a region inside the subject. An imaging element picks up the reflected light, i.e., a reflected image, and obtains image information. Thus obtained image information is transmitted by radio by a transmitting circuit.

SUMMARY OF THE INVENTION

A body-insertable apparatus according to one aspect of the present invention is inserted into a subject and obtains information of an inside of the subject, and includes an illuminating unit that outputs an illumination light to illuminate the inside of the subject; an imaging unit that obtains image information of the inside of the subject which is illuminated by the illuminating unit; a radio transmitting unit that transmits information of the inside of the subject by radio; a clock generating unit that generates a clock for obtainment of the image information by the imaging unit; and a correcting unit that corrects a clock for radio transmission by the radio transmitting unit based on the clock generated by the clock generating unit.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Exemplary embodiments of a body-insertable apparatus according to the present invention will be described in detail below with reference to FIGS. 1 to 5. It should be noted, however, that the present invention is not limited by the embodiments, and various modification can be made without departing from a scope of the present invention.

Figure 1:
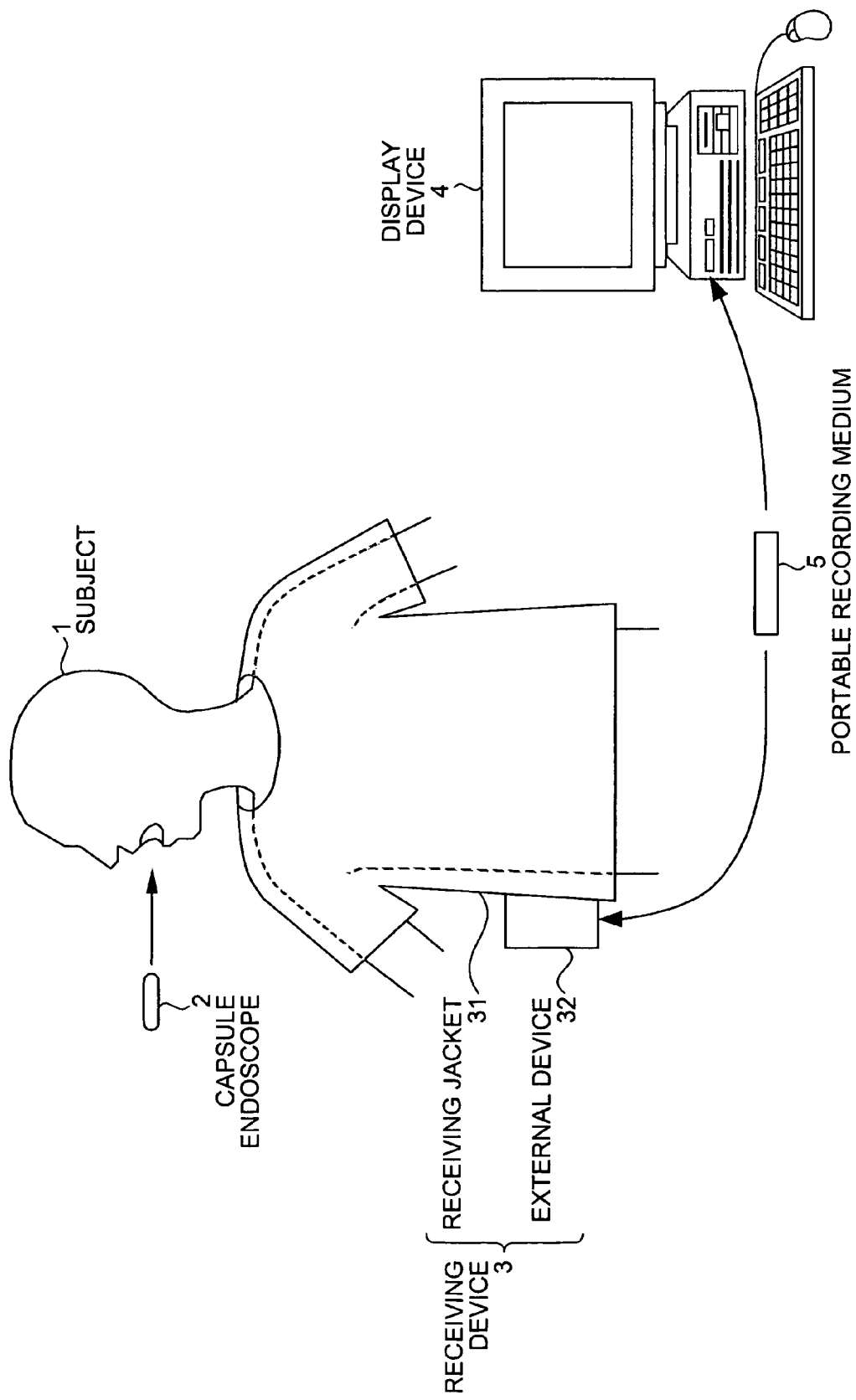
FIG. 1 is a schematic diagram of an overall structure of a wireless intra-subject information obtaining system including a body-insertable apparatus according to a first embodiment.

FIG. 1 is a schematic diagram of an overall structure of a wireless intra-subject information obtaining system including a body-insertable apparatus of a first embodiment. In a following description of the wireless intra-subject information obtaining system, a capsule endoscope will be described as an example of the body-insertable apparatus. In FIG. 1, the wireless intra-subject information obtaining system includes a receiving device 3 which has a radio receiving function, and a capsule endoscope (body-insertable apparatus) 2 which is insertable inside a subject 1, images inside a body cavity, and transmits data such as video signals to the receiving device 3. Further, the wireless intra-subject information obtaining system includes a display device 4 which displays an image inside the body cavity based on the video signals received by the receiving device 3, and a portable recording medium 5 which serves for data delivery between the receiving device 3 and the display device 4. The receiving device 3 includes a receiving jacket 31 which is worn by the subject 1 and an external device 32 which processes received radio signals, for example.

The display device 4 serves to display the image inside the body cavity obtained by the capsule endoscope 2. The display device 4 has a structure like a workstation and displays an image based on data obtained from the portable recording medium 5. Specifically, the display device 4 may directly display an image like a CRT display, or a liquid crystal display. Alternatively, the display device 4 may output an image on other media, like a printer.

The portable recording medium 5 can be detachably attached to the external device 32 and the display device 4. When the portable recording medium 5 is attached to one of the external device 32 and the display device 4, information can be output from or recorded in the portable recording medium 5. In the first embodiment, while the capsule endoscope 2 travels inside the body cavity of the subject 1, the portable recording medium 5 is attached to the external device 32 and records data transmitted from the capsule endoscope 2. After the capsule endoscope 2 is discharged from the subject 1, i.e., after the imaging inside the subject 1 is completed, the portable recording medium 5 is removed from the external device 32 and attached to the display device 4. Then, the display device 4 reads out the data recorded in the portable recording medium 5. When the data delivery between the external device 32 and the display device 4 is carried out with the portable recording medium 5 such as a Compact Flash (registered trademark) memory, the subject 1 can move more freely during the imaging, compared with a time when the external device 32 and the display device 4 are directly connected by a cable. In the first embodiment, the portable recording medium 5 is employed for the data delivery between the external device 32 and the display device 4. The present invention, however, is not limited thereto. For example, another type of recording unit, such as a hard disc may be incorporated in the external device 32, and the external device 32 and the display device 4 may be connected by a cable or by radio for data delivery.

Figure 2:
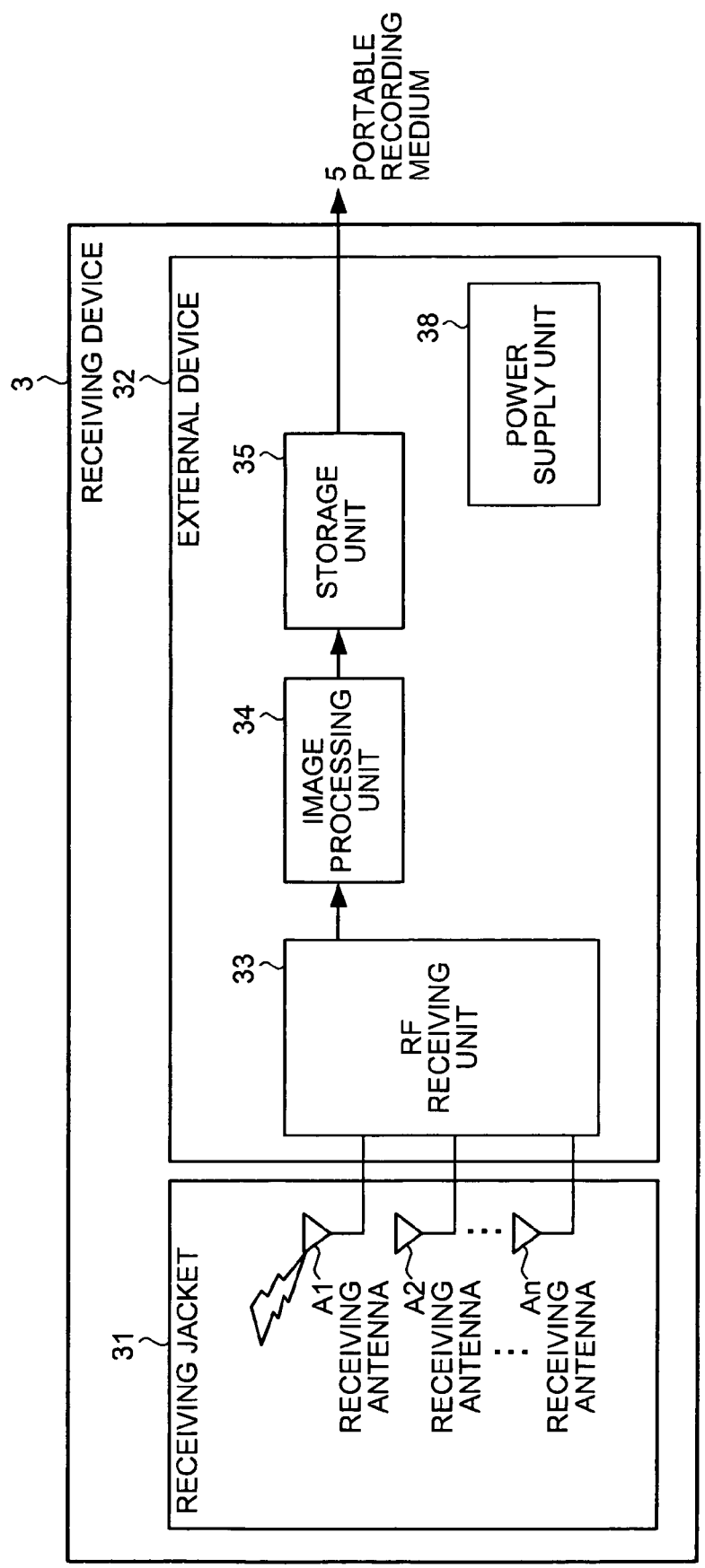
FIG. 2 is a block diagram of an internal structure of a receiving device according to the first embodiment shown in FIG. 1.

A structure of the receiving device will be described below with reference to a block diagram of FIG. 2. The receiving device 3 has a function of receiving the image data of inside the body cavity transmitted by radio from the capsule endoscope 2. As shown in FIG. 2, the receiving device 3 includes the receiving jacket 31 and the external device 32. The receiving jacket 31 is formed so that the subject 1 can wear the jacket 31, and provided with receiving antennae A1 to An. The external device 32 processes radio signals, for example, received by the receiving jacket 31. Here, the receiving antennae A1 to An may be directly attached to an outer surface of the subject 1, rather than attached to the receiving jacket 31. Alternatively, the receiving antennae A1 to An may be detachably attached to the receiving jacket 31.

The external device 32 includes an RF receiving unit 33, an image processing unit 34, a storage unit 35, and processes the radio signals sent from the capsule endoscope 2. The RF receiving unit 33 performs a predetermined signal processing such as demodulation on the radio signals received by the receiving antennae A1 to An, and extracts image data obtained by the capsule endoscope 2 from the radio signals. The image processing unit 34 performs necessary image processing on the extracted image data. The storage unit 35 serves to store the image data after the image processing. In the first embodiment, the image data is stored in the portable recording medium 5 via the storage unit 35. The external device 32 further includes a power supply unit 38 which is provided with a predetermined capacitor or an AC power adapter. Each of the elements in the external device 32 uses electricity supplied from the power supply unit 38 as driving energy.

Figure 3:
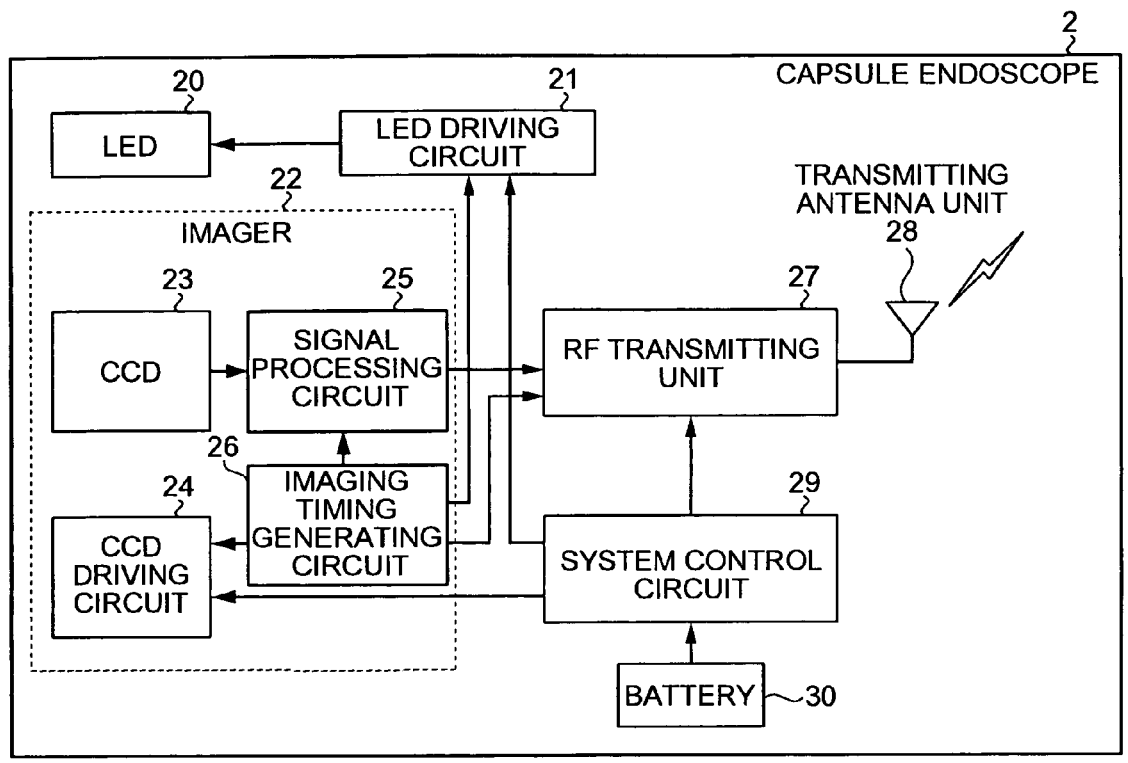
FIG. 3 is a block diagram of an internal structure of a capsule endoscope according to the first embodiment shown in FIG. 1.
Figure 4:
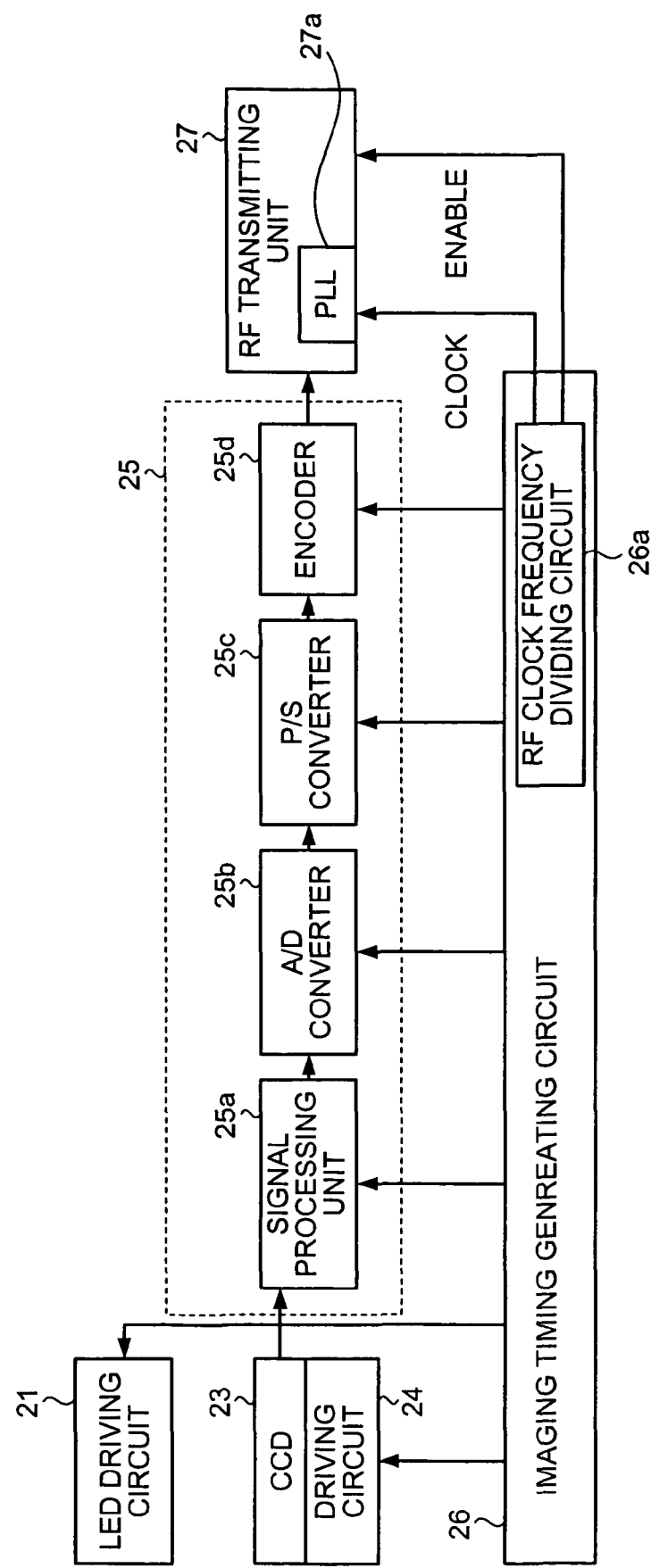
FIG. 4 is a block diagram of a structure of an imaging timing system shown in FIG. 3.

A structure of the capsule endoscope will be described with reference to a block diagram of FIG. 3. The capsule endoscope 2 includes, as shown in the block diagram of FIG. 3, a light emitting diode (LED) 20, an LED driving circuit 21, a charge coupled device (CCD) 23, a CCD driving circuit 24, a signal processing circuit 25, and an imaging timing generating circuit 26. The LED 20 serves as an illuminating unit that irradiates an examined region inside the body cavity of the subject 1 with light. The LED driving circuit 21 controls a driven state of the LED 20. The CCD 23 serves as an imaging unit that picks up reflected light from the region illuminated by the LED 20 as an image inside the body cavity. The CCD driving circuit 24 controls a driven state of the CCD 23. The signal processing circuit 25 processes an image output from the CCD 23 into image information of a desired form. The imaging timing generating circuit 26 serves as a clock generating unit that outputs a reference clock to set a driving timing such as a lighting timing of the LED 20 and an imaging timing of the CCD 23. The capsule endoscope 2 further includes an RF transmitting unit 27 and a transmitting antenna unit 28. The RF transmitting unit 27 modulates the picked up image signal into an RF signal. The transmitting antenna unit 28 serves as a radio transmitting unit that transmits the RF signal output from the RF transmitting unit 27 by radio. Further, the capsule endoscope 2 includes a system control circuit 29 that controls operations of the LED driving circuit 21, the CCD driving circuit 24, and the RF transmitting unit 27. The CCD 23, the CCD driving circuit 24, the signal processing circuit 25, and the imaging timing generating circuit 26 are collectively referred to as an imager 22. The capsule endoscope 2 having the above elements operates so as to obtain the image information of the examined region illuminated by the LED 20 by the CCD 23 based on the reference clock which sets a desired imaging timing, while the capsule endoscope 2 is inside the subject 1. The obtained image information is processes by the signal processing circuit 25 based on the reference clock, and converted into the RF signal by the RF transmitting unit 27, and sent outside the subject 1 by the transmitting antenna unit 28.

The imaging timing generating circuit 26 incorporates a circuit (not shown) that generates a reference clock, and outputs the reference clock to the LED driving circuit 21, the CCD driving circuit 24, and the signal processing circuit 25 to set the driving timing. Further, the imaging timing generating circuit 26 includes an RF clock frequency dividing circuit 26a as a frequency dividing unit that divides the frequency of the reference clock, and outputs a frequency-divided clock from the RF clock frequency dividing circuit 26a to the RF transmitting unit 27. The reference clock output from the imaging timing generating circuit 26 is produced with high accuracy so as to function as a reference for a minute timing of a driving signal for imaging elements, and an absolute value of tolerance for frequency fluctuation is set small. In the first embodiment, the frequency of the highly accurate reference clock which sets the imaging timing of the CCD is divided by the RF clock frequency dividing circuit 26a to output an RF clock. Thus, the RF clock for phase synchronization of an RF reference clock is generated. The generated RF clock is output to the RF transmitting unit 27. Thus, the transmission carrier wave can be stably oscillated. Therefore, a separate installment of a highly accurate clock unit inside the RF transmitting unit is not necessary.

Further, after the image signal is output from the CCD 23, the signal processing unit 25a of the signal processing circuit 25 carries out a desired signal processing on the image signal. Then, the resulting signal is converted into a digital signal by an A/D conversion in the A/D converter 25b. Further, the resulting digital signal is converted into a serial signal by a parallel/serial conversion in the P/S converter 25c. Then the resulting serial signal is encoded in the encoder 25d and supplied to the RF transmitting unit 27.

Figure 5:
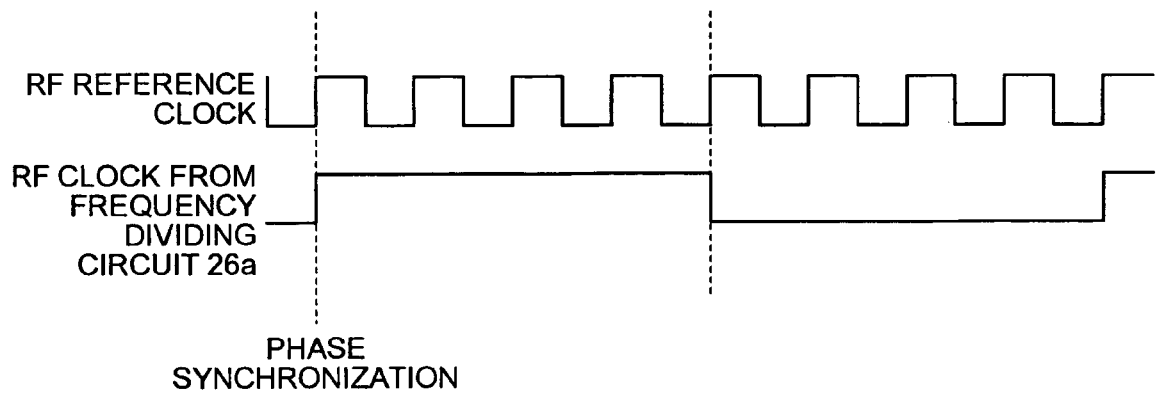
FIG. 5 is a timing chart illustrating an operation of the imaging timing system shown in FIG. 4.
Figure 6:
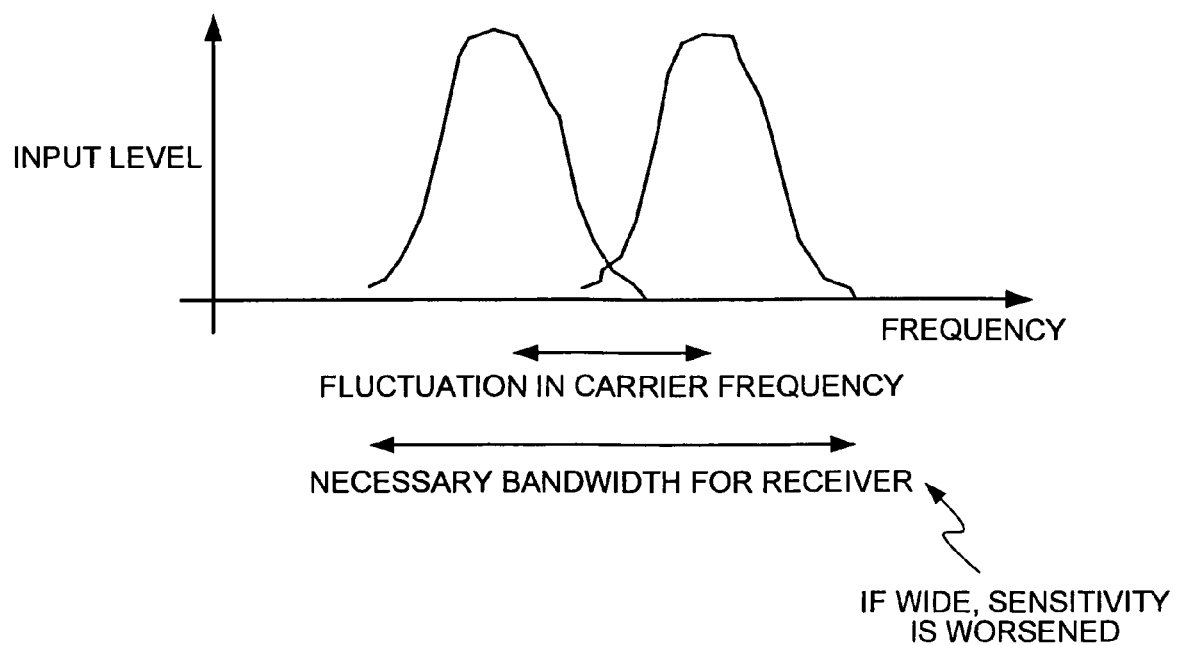
FIG. 6 is a diagram illustrating a conventionally observed fluctuation in a frequency of a transmission carrier wave.

The RF transmitting unit 27 has a PLL circuit 27a which serves as a synchronizing unit that takes in a frequency-divided clock supplied from the RF clock frequency dividing circuit 26a. Specifically, as shown in FIG. 5, for example, the RF clock frequency dividing circuit 26a outputs an RF clock which is obtained by dividing the frequency of the reference clock for imaging by four, and the PLL circuit 27a carries out a phase locking based on the RF clock, so that a phase of the RF reference clock is synchronized with the phase of the RF clock at a rising (or a falling) of the RF clock, thereby oscillating the transmission carrier wave in a stable manner and suppressing the fluctuation in the transmission frequency. Thereafter, the radio transmission of the image information is carried out.

As described above, in the first embodiment, the imager outputs the RF clock with accurate and stable frequency to the RF transmitting unit, and the phase of the RF reference clock is synchronized with the phase of the RF clock. Thus, the RF reference clock can be oscillated in a stable manner and the fluctuation in the transmission frequency of the transmission carrier wave can be suppressed. Therefore, the passing band of the bandpass filter on the side of the receiving device can be set to a narrow band. Thus, the receiving device can receive image information with little noise and with good sensitivity.

Further, in the first embodiment, a clock is generated by frequency division of the imaging reference clock which sets the imaging timing of the CCD. The generated clock is output to the RF transmitting unit for the correction of the RF reference clock. Therefore, an amount of output electric current of an output pin of an integrated circuit (IC) that forms a part of the imager 22 can be made small, and power consumption for clock output can also be reduced.

In the first embodiment, during the driving timing of the CCD, for example, the output of the RF clock from the frequency dividing circuit may be stopped, and the driven state of the CCD may be notified to the RF transmitting unit 27 by enable signals. In response to the operation of the imaging timing generating circuit 26, the RF transmitting unit can stop the driving. Thus, the power consumption of the overall system can be reduced. In addition, if the output of the RF clock is stopped while there is no input of the image signals and there is no need of driving of the RF transmitting unit 27, the power consumption can be further reduced. Still further, to allow for the synchronization of the RF clock and the RF reference clock, the RF clock frequency dividing circuit can be set so that the RF clock has a higher frequency than a transmission frequency of one pixel of the CCD. Still alternatively, the RF reference clock of a high frequency band may directly be generated by frequency dividing, and supplied to the RF transmitting unit.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A body-insertable apparatus which is inserted into a subject and obtains information of an inside of the subject, comprising:
    an illuminating unit that outputs an illumination light to illuminate the inside of the subject;
    an imaging unit that obtains image information of the inside of the subject which is illuminated by the illuminating unit;
    a radio transmitting unit that transmits information of the inside of the subject by radio;
    a clock generating unit that generates a clock for obtainment of the image information by the imaging unit; and
    a correcting unit that corrects a clock for radio transmission by the radio transmitting unit based on the clock generated by the clock generating unit;
    wherein the clock generating unit includes a frequency dividing unit that divides a frequency of the clock generated, and the clock generating unit outputs a clock after a frequency dividing by the frequency dividing unit to the radio transmitting unit and the clock generating unit stops supplying the clock to the radio transmitting unit during driving timing of the imaging unit.

2. A body-insertable apparatus which is inserted into a subject and obtains information of an inside of the subject, comprising:
    an illuminating unit that outputs an illumination light to illuminate the inside of the subject;
    an imaging unit that obtains image information of the inside of the subject which is illuminated by the illuminating unit;
    a radio transmitting unit that transmits information of the inside of the subject by radio;
    a clock generating unit that generates a clock for obtainment of the image information by the imaging unit; and
    a correcting unit that corrects a clock for radio transmission by the radio transmitting unit based on the clock generated by the clock generating unit;
    wherein the clock generating unit includes a frequency dividing unit that divides a frequency of the clock generated, and the clock generating unit outputs a clock after a frequency dividing by the frequency dividing unit to the radio transmitting unit,
    the clock generating unit stops supplying the clock to the radio transmitting unit while the radio transmitting unit is not operating.

3. A method of obtaining information of an inside of a subject by a body-insertable apparatus which is inserted into the subject, comprising:
    outputting an illumination light to illuminate the inside of the subject;
    imaging image information of the inside of the subject illuminated, by an imaging unit;
    transmitting information of the inside of the subject by radio, by a radio transmitting unit;
    generating a clock for the imaging of the image information;
    correcting a clock for the transmitting based on the clock for the imaging;
    dividing a frequency of the clock for the imaging;
    outputting a clock after the dividing of the frequency to the radio transmitting unit; and
    stopping outputting the clock for the transmitting during driving timing of the imaging unit.

4. A method of obtaining information of an inside of a subject by a body-insertable apparatus which is inserted into the subject, comprising:
    outputting an illumination light to illuminate the inside of the subject;
    imaging image information of the inside of the subject illuminated, by an imaging unit;
    transmitting information of the inside of the subject by radio, by a radio transmitting unit;
    generating a clock for the imaging of the image information;

correcting a clock for the transmitting based on the clock for the imaging;

dividing a frequency of the clock for the imaging;

outputting a clock after the dividing of the frequency to the radio transmitting unit; and stopping outputting the clock for the transmitting while the radio transmitting unit is not operating.

5. A body-insertable apparatus which is inserted into a subject and obtains information of an inside of the subject, comprising:

an illuminating unit that outputs an illumination light to illuminate the inside of the subject;

an imaging unit that obtains image information of the inside of the subject which is illuminated by the illuminating unit;

a radio transmitting unit that transmits information of the inside of the subject by radio;

a clock generating unit that generates a clock for obtainment of the image information by the imaging unit;

an RF clock frequency dividing unit that divides the frequency of the clock to output a frequency-divided clock; and a PLL unit that takes in the frequency-divided clock supplied from the RF clock frequency dividing unit, and carries out a phase locking based on the frequency-divided clock to oscillate a transmission carrier wave for the radio transmitting unit, wherein the clock generating unit stops supplying the clock to the radio transmitting unit while the radio transmitting unit is not operating.

6. The body-insertable apparatus according to claim 1, wherein the clock generating unit stops supplying the clock to the radio transmitting unit while the radio transmitting unit is not operating.

7. A method of obtaining information of an inside of a subject by a body-insertable apparatus which is inserted into the subject, comprising:

outputting an illumination light to illuminate the inside of the subject;

imaging image information of the inside of the subject illuminated, by an imaging unit;

transmitting information of the inside of the subject by radio, by a radio transmitting unit;

generating a clock for the imaging of the image information;

dividing the frequency of the clock to output a frequency-divided clock by an RF clock frequency dividing unit;

taking in the frequency-divided clock supplied from the RF clock frequency dividing unit, and carrying out a phase locking based on the frequency-divided clock to oscillate a transmission carrier wave for the radio transmitting unit; and stopping outputting the clock for the transmitting while the radio transmitting unit is not operating.

8. The method according to claim 3, further comprising stopping outputting the clock for the transmitting while the radio transmitting unit is not operating.

* * * * *